United States Patent
Hansen

(10) Patent No.: US 10,105,518 B2
(45) Date of Patent: Oct. 23, 2018

(54) SOFT LOCK WIRE GUIDE AND NEURO-SURGERY ASSEMBLY USING SAME

(71) Applicant: Cook Medical Technologies LLC, Bloomington, IN (US)

(72) Inventor: Palle Munk Hansen, Bjaeverskov (DK)

(73) Assignee: Cook Medical Technologies LLC, Bloomington, IN (US)

( * ) Notice: Subject to any disclaimer, the term of this patent is extended or adjusted under 35 U.S.C. 154(b) by 363 days.

(21) Appl. No.: 14/944,570

(22) Filed: Nov. 18, 2015

(65) Prior Publication Data
US 2016/0250449 A1 Sep. 1, 2016

Related U.S. Application Data

(60) Provisional application No. 62/121,139, filed on Feb. 26, 2015.

(51) Int. Cl.
*A61M 25/09* (2006.01)
*A61M 25/01* (2006.01)
*A61M 25/00* (2006.01)

(52) U.S. Cl.
CPC ......... *A61M 25/09* (2013.01); *A61M 25/0138* (2013.01); *A61M 2025/0042* (2013.01); *A61M 2025/09008* (2013.01); *A61M 2025/0915* (2013.01); *A61M 2025/09116* (2013.01); *A61M 2210/0693* (2013.01)

(58) Field of Classification Search
CPC ........ A61M 25/09; A61M 2025/09008; A61M 2025/09116; A61M 2210/0693; A61M 2025/0915; A61M 25/0138; A61M 2025/0042
See application file for complete search history.

(56) References Cited

U.S. PATENT DOCUMENTS

| | | | |
|---|---|---|---|
| 6,146,339 A | 11/2000 | Biagtan et al. | |
| 7,914,466 B2 | 3/2011 | Davis et al. | |
| 8,728,010 B2 | 5/2014 | Hirshman | |
| 2006/0074372 A1* | 4/2006 | Haga | A61M 25/0054 604/19 |
| 2009/0187163 A1 | 7/2009 | Uihlein | |
| 2013/0046285 A1 | 2/2013 | Griffin et al. | |
| 2013/0096535 A1 | 4/2013 | Gregorich et al. | |

FOREIGN PATENT DOCUMENTS

EP 3061487 A1 * 8/2016 ............ A61M 25/09

* cited by examiner

*Primary Examiner* — Amber Stiles
(74) *Attorney, Agent, or Firm* — Liell & McNeil

(57) ABSTRACT

A neuro-surgery assembly includes a neuro-catheter slidably received over a wire guide. The wire guide includes an inner tube positioned within an elongate hollow tube that includes a pattern of openings at its distal segment to provide an atraumatic tip for reaching sensitive locations in a brain. The wire guide is changeable between a stiff condition in which the inner tube is pressurized and a soft condition in which the inner tube is depressurized. The user may switch between the stiff and soft conditions to negotiate the tortuous pathway to a brain treatment site without a need to swap out to a different wire guide to support advancement of the neuro-catheter.

13 Claims, 3 Drawing Sheets

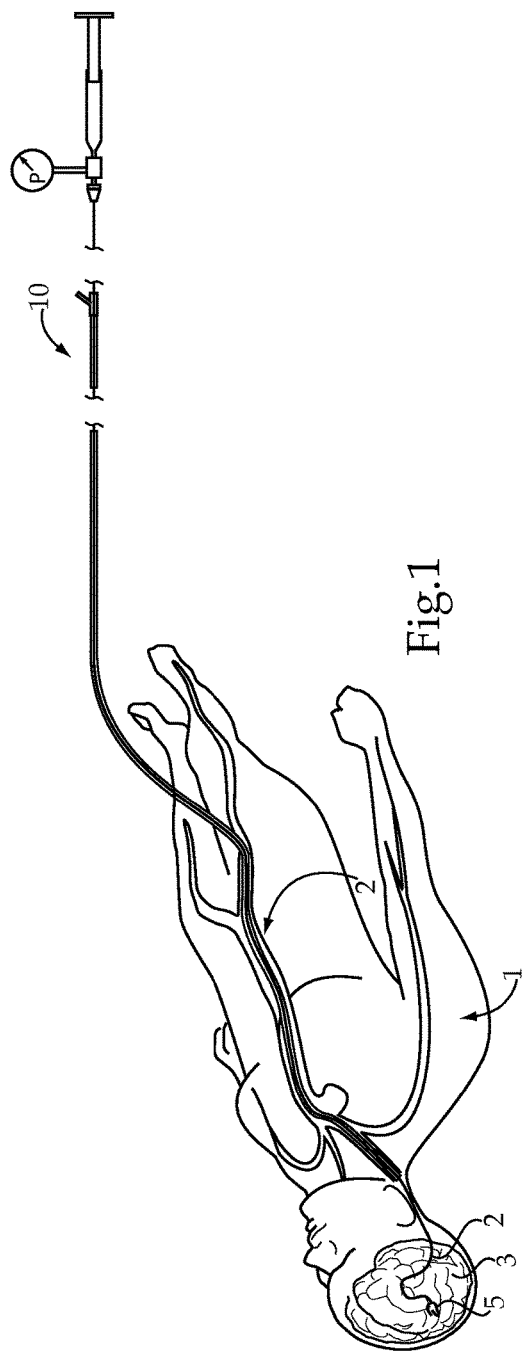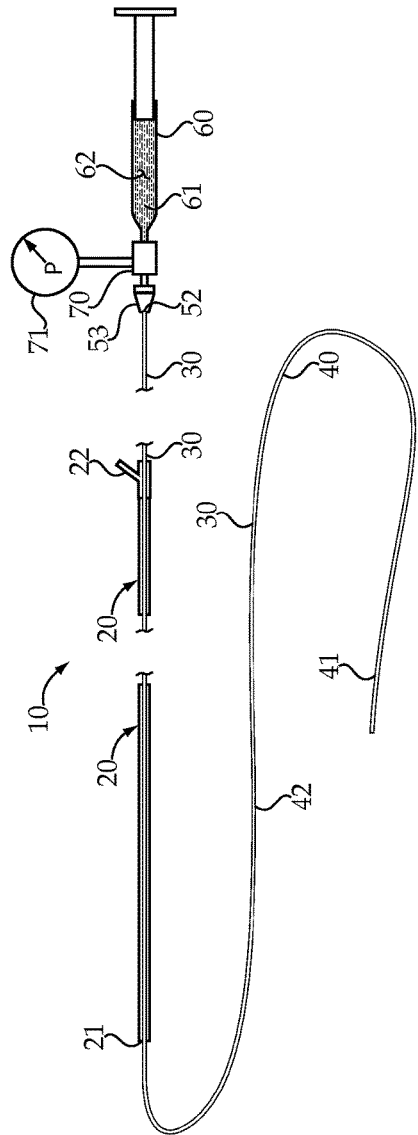

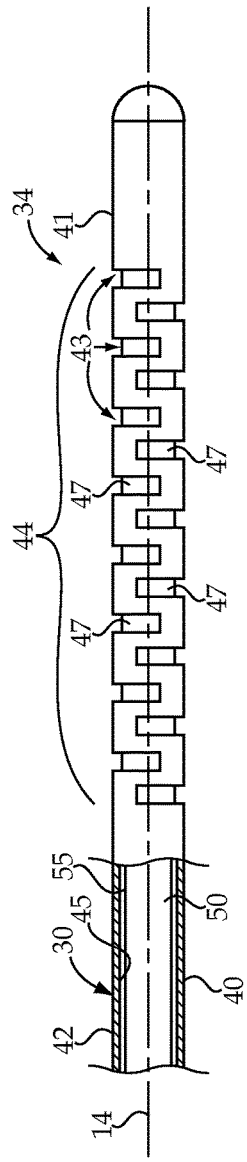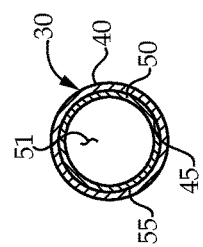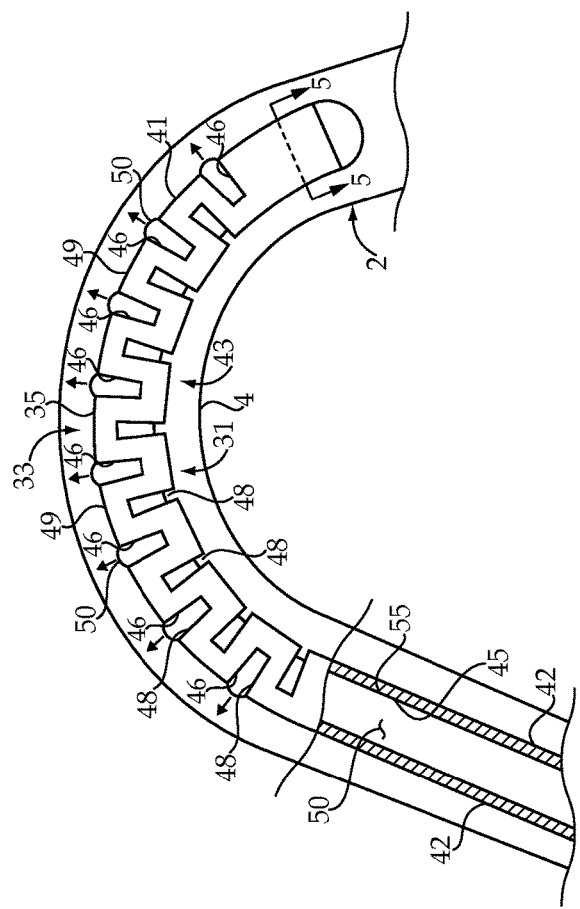

SOFT LOCK WIRE GUIDE AND NEURO-SURGERY ASSEMBLY USING SAME

TECHNICAL FIELD

The present disclosure relates generally to neuro-surgery, and more particularly to a wire guide changeable at will between stiff and soft conditions.

BACKGROUND

Some neuro-surgery treatments require that a distal end of a neuro-catheter be positioned in close proximity to a treatment site in a brain. Prior to the neuro-catheter reaching the treatment site, a wire guide must often first be properly positioned in proximity to the treatment site. Due to the tiny size and sensitivity of passageways within the brain, very soft wire guides must often be used to navigate the tortuous pathway to the treatment site. However, these extremely soft and slender wire guides may not be stiff enough to support the neuro-catheter when being slid over the wire guide to the treatment site. Thus, the physician may often have to repeatedly switch between relatively soft and stiff wire guides to successfully negotiate each of several sharp turns on the way to the treatment site. This switching back and forth between different wire guides can extend the duration of the surgery, increase risks to patients and increase medical device costs.

The present disclosure is directed toward overcoming one or more of the problems set forth above.

SUMMARY

In one aspect, a wire guide includes an inner tube with a closed distal end positioned inside an elongate hollow tube with a distal segment that defines a plurality of openings. The openings are arranged in a pattern so that a distal segment of the elongate hollow tube is more flexible that a proximal segment. An inflation device with a reservoir of liquid is fluidly connected to a proximal end of the inner tube. The wire guide has a stiff condition in which the inner tube is pressurized by the liquid causing an external surface of the inner tube to bear against an internal surface of the elongate hollow tube. The wire guide has a soft condition in which the inner tube is de-pressurized causing the external surface of the inner tube to be at least partially out of contact with the internal surface of the elongate hollow tube. The inner tube protrudes into a portion, which is less than all, of the plurality of openings when the distal segment is in a curved configuration and the wire guide is in the stiff condition. A shape of each of the plurality of openings changes responsive to flexure of the distal segment away from a straight configuration.

In another aspect, a neuro-surgery assembly includes a neuro-catheter slidably received over the wire guide. The neuro-surgery assembly has an approach arrangement in which the wire guide is in the stiff condition and a distal end of the neuro-catheter is located proximal to the distal segment. The neuro-surgery assembly as an arrival arrangement in which the wire guide is in the stiff condition and the distal segment of the wire guide is inside the neuro-catheter. The neuro-surgery assembly has a pre-treatment arrangement in which the wire guide is in the soft condition, and the distal segment is withdrawn into the neuro-catheter and separated from the distal end by a withdrawal distance.

The neuro-surgery assembly may be operated by advancing the wire guide around a turn of a tortuous pathway toward a treatment site in a brain while the wire guide is in the soft condition. The wire guide may then be stopped in the turn with the distal segment in a curved configuration. The neuro-catheter is then slid over the wire guide toward the turn. The wire guide is changed from the soft condition to the stiff condition when a distal end of the neuro-catheter is proximal to the distal segment. The neuro-catheter is then slid around the turn and over the distal segment toward the treatment site. The wire guide is then changed from a stiff condition back to the soft condition. The neuro-catheter is stopped at the treatment site and maintained at the treatment site while the wire guide is withdrawn in the soft condition from the neuro-catheter.

BRIEF DESCRIPTION OF THE DRAWINGS

FIG. 1 is a perspective schematic view of a neuro-surgery process using the neuro-surgery assembly of the present disclosure;

FIG. 2 is a schematic view of a neuro-surgery assembly according to the present disclosure;

FIG. 3 shows a distal portion of the wire guide of FIG. 2 in a soft condition and a straight configuration;

FIG. 4 is a side view of the wire guide of FIG. 3 in the stiff condition and the curved configuration;

FIG. 5 is a sectioned view of the wire guide of FIG. 4 as viewed along section lines 5-5.

DETAILED DESCRIPTION

Figure 6:
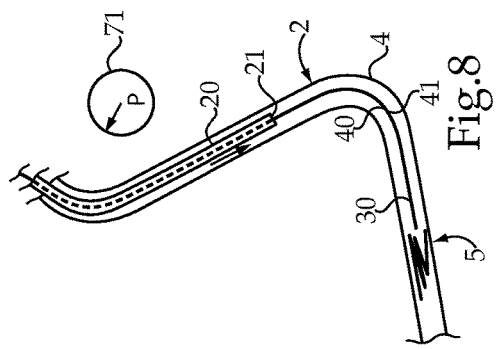
FIG. 6 is a schematic view a terminal segment of a tortuous pathway to a treatment site.
Figure 9:
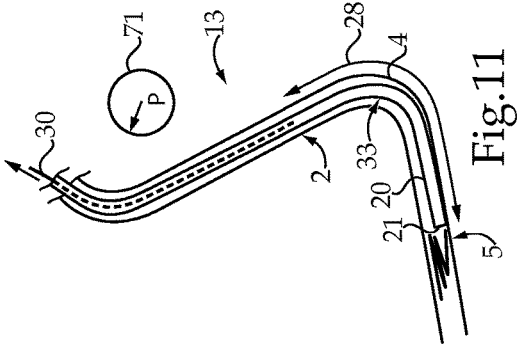
FIG. 9 is the terminal segment with the neuro-surgery assembly in an approach arrangement with the wire guide in the stiff condition.

Referring initially to FIGS. 1-5, a neuro-surgery assembly 10 includes a neuro-catheter 20 (less than or equal to 3 French) slidably received over a wire guide 30. The neuro-catheter includes a distal end 21 and terminates at its proximal end with a fitting 22, which may be my suitable fitting known in the art. The wire guide 30 includes an elongate hollow tube 40 with a distal segment 41 that defines a plurality of openings 43 arranged in a pattern 44 so that the distal segment 41 is more flexible than a proximal segment 42 of the elongate hollow tube 40. An inner tube 50 is positioned inside the elongate hollow tube 40, and has a closed distal end 51. An inflation device 60 has a reservoir 61 of liquid 62 fluidly connected to a proximal end 52 of the inner tube 50. The wire guide 30 has a stiff condition 31 in which the inner tube 50 is pressurized by the liquid 62 causing an external surface 55 of the inner tube 50 to bear against an internal surface 45 of the elongate hollow tube 40. Liquid 62 may be saline, and may include a radiopaque additive. The wire guide can be changed from the stiff condition 31 (FIG. 4) to a soft condition 32 (FIG. 3) in which the inner tube 50 is depressurized causing the external surface 55 of the inner tube 50 to be at least partially out of contact with the internal surface 45 of the elongate hollow tube 40. Elongate hollow tube 40 may be made from any suitable material known in the art, including plastics or even metal alloys. The inner tube 50 may be made from a suitable polymer. Although not necessary, the neuro-surgery assembly 10 may include a fitting 70 with a pressure gauge 71 to indicate the pressure of liquid 62 at any given time. The proximal end 52 may include a fitting 53 for fluid connection to inflation device 60 in any suitable manner known in the art.

As best shown in FIG. 4, the inner tube 50 protrudes into a portion 46, which is less than all, of the plurality of openings 43 when the distal segment 41 is in a curved configuration 33 and the wire guide 30 is in the stiff condition 31. Thus, those skilled in the art will appreciate that a shape 48 of each of the plurality of openings 43 changes responsive to flexure of the distal segment 41 away from the straight configuration 34. Thus, one could expect the portion of the openings 46 on the outer radius 35 to enlarge in width while a shape 48 of the openings 43 on the inner radius may decrease in size, as best shown in FIG. 4. In the illustrated embodiment, the openings 43 take the form of slots 47, but those still in the art will appreciate that different sized and shaped openings would also fall within the scope of the present disclosure. In the illustrated embodiment, slots 47 may be oriented perpendicular to a central axis 14 of elongate hollow tube 40, but other orientations would also fall within the intended scope of the present disclosure. Although not necessary, inner tube 50 may protrude through one or more of the plurality of openings 46 radially beyond an outer surface 49 of the elongate hollow tube 40 that surrounds the relevant openings 46 when the distal segment 41 is in the curved configuration 33 (FIG. 4) and the inner tube 50 is pressurized as per the stiff condition 31.

INDUSTRIAL APPLICABILITY

The present disclosure finds general applicability in any wire guide. The present disclosure finds specific applicability for neuro-surgery applications.

Figure 7:
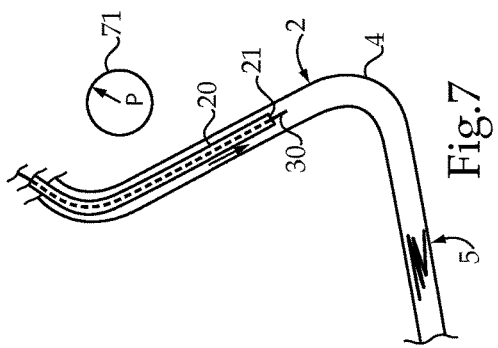
FIG. 7 is the terminal segment of FIG. 6 after the neuro-catheter and wire guide of the present disclosure prepare for a final turn prior to the treatment site.
Figure 10:
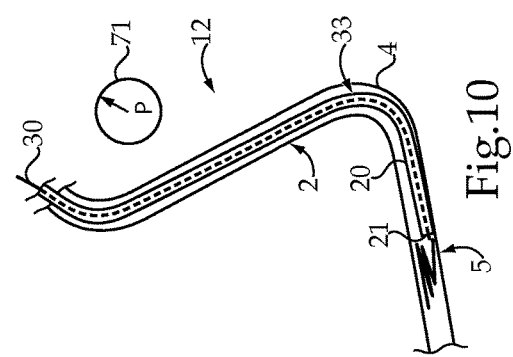
FIG. 10 is a view of the terminal segment in an arrival arrangement.
Figure 8:
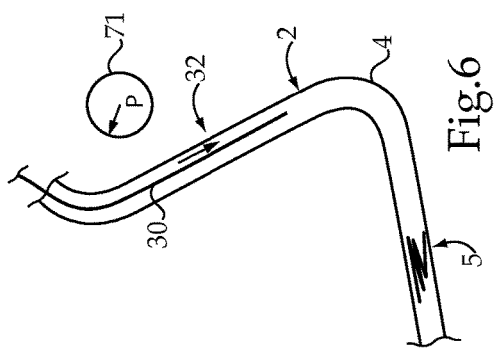
FIG. 8 is the terminal segment of FIG. 6 after the wire guide has arrived at the treatment site.
Figure 11:
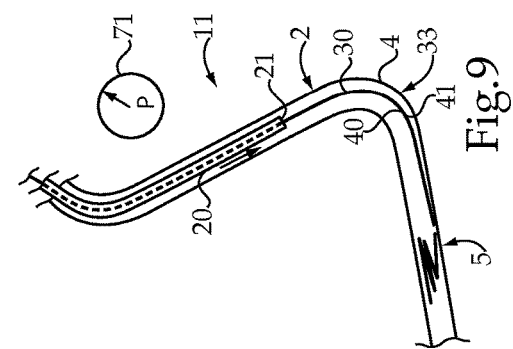
FIG. 11 is a view of the terminal segment with the neuro-surgery assembly in a pre-treatment arrangement with the wire guide being withdrawn in a soft condition.

Referring again to FIG. 1-5 and in addition to FIGS. 6-11, a method of operating the neuro-surgery assembly 10 is illustrated. The illustrations of FIGS. 6-10 show a terminal segment of a tortuous pathway 2 to a treatment site 5 in a brain 3 of a patient 1. Those skilled in the art will appreciate that a surgeon may, in the past, have had to repeatedly switch between relatively stiff and soft wire guides in order to incrementally move a neuro-catheter 20 to a treatment site 5 in the patient's brain 3. However, by utilizing the wire guide 30 of the present disclosure, the physician may instead change the wire guide between a stiff condition 31 and a soft condition 32 in order to achieve the same purpose while utilizing only a single wire guide 30 in order to advance the neuro-catheter 20 to the treatment site 5. FIG. 6 shows wire guide 30 being advanced along tortuous pathway 2 while in a soft condition as evidenced by the low pressure indication on gauge 71. After rounding the previous turn, the wire guide 30 may be placed in a stiff condition 31 and the neuro-catheter 20 advanced over wire guide 30 to achieve comparable positioning as shown in FIG. 7. Next, the wire guide 30 may be changed from the stiff condition 31 back to the soft condition 32 as evidenced by pressure gauge 71 in FIG. 8. The wire guide 30 may then be advanced around turn 4 of tortuous pathway 2 toward treatment site 5 in the patients brain 3 while the wire guide 30 is in the soft condition 32. Next, at FIG. 9, the neuro-surgery assembly 10 may have an approach arrangement 11 in which the wire guide 30 is in the stiff condition 31 and the distal end 21 of neuro-catheter 20 is located proximal to the distal segment 41 of elongate hollow tube 40. With wire guide 30 in the stiff condition 31, wire guide 30 may be sufficiently stiff to allow neuro-catheter 20 to be maneuvered from the approach arrangement 11 to the arrival arrangement 12 as shown in FIG. 10 in which the wire guide 30 is in a stiff condition 31 and the distal segment 41 of the wire guide 30 is positioned inside the neuro-catheter 20. Thus, when transitioning from the approach arrangement 11 to the arrival arrangement 12, the neuro-catheter 20 will be slid over wire guide 20 toward and around turn 4 and then over distal segment 41 to arrive at treatment site 5. After stopping neuro-catheter 20 at treatment site 5, the wire guide 30 may be changed back from the stiff condition 31 to the soft condition 32. FIG. 11 shows neuro-surgery assembly 10 being transitioned to a pre-treatment arrangement 13 in which the wire guide 30 is in the soft condition 32, and the distal segment 41 is withdrawn into neuro-catheter 20 and separated from the distal end 21 by a withdrawal distance 28. Those skilled in the art will appreciate that FIG. 11 shows wire guide 30 being withdrawn from neuro-catheter 20 so that the treatment of treatment site 5 may commence using neuro-catheter 20 properly positioned as shown. For example, treatment site 5 may comprise a stenosis of a type known in the art, and neuro-catheter 20 may be utilized to deliver a stenosis dissolving treatment fluid to treatment site 5, or some other treatment known in the art.

Although the illustrations of FIGS. 6-11 show how the neuro-surgery assembly 10 of the present disclosure successfully maneuvers a turn 4 in a tortuous path 2 to a treatment site 5, those skilled in the art will appreciate that the wire guide 30 may be changed between the soft condition 32 and the stiff condition 31 a plurality of times while wire guide 30 is maneuvered from an entry site in the patient body 1 to the treatment site 5 within the brain 3. Those skilled in the art will appreciate that wire guide 30 may be easily and atraumatically advanced around turns in the patient's anatomy while in the soft condition 32, but may need to be changed to the stiff condition 31 in order to support advancement of neuro-catheter 20 around each successive turn on the way to a treatment site 5. Although the present disclosure does not rule out the physician changing between different wire guides while attempting to approach treatment site 5 with a neuro-catheter 20, many neuro-surgery procedures may allow for the use of a single wire guide 30 according to the present disclosure in order to gain access all the way to the treatment site. As such, one could expect the wire guide 30 to stop at treatment site 5. Although not necessary, the inflation liquid 62 may include a radiopaque contrast in order to allow the physician to quickly assess the location and track the progress of wire guide 30 in a manner well known in the art. For purposes of the present disclosure, a neuro-catheter means a catheter of three French or less.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:
1. A neuro-surgery assembly comprising:
a neuro-catheter slidably received over a wire guide;
the wire guide comprising:
an elongate hollow tube with a distal segment that defines a plurality of openings arranged in a pattern so that the distal segment is more flexible than a proximal segment of the elongate hollow tube;

an inner tube positioned inside the elongate hollow tube and having a closed distal end;

an inflation device with a reservoir of liquid fluidly connected to a proximal end of the inner tube;

the wire guide having a stiff condition in which the inner tube is pressurized by the liquid causing an external surface of the inner tube to bear against an internal surface of the elongate hollow tube;

the wire guide having a soft condition in which the inner tube is depressurized causing the external surface of the inner tube to be at least partially out of contact with the internal surface of the elongate hollow tube;

wherein the inner tube protrudes into a portion, which is less than all, of the plurality of openings when the distal segment is in a curved configuration and the wire guide is in the stiff condition;

the neuro-surgery assembly having an approach arrangement in which the wire guide is in the stiff condition and a distal end of the neuro-catheter is located proximal to the distal segment;

the neuro-surgery assembly having an arrival arrangement in which the wire guide is in the stiff condition and the distal segment of the wire guide is inside the neuro-catheter; and the neuro-surgery assembly having a pretreatment arrangement in which the wire guide is in the soft condition, and the distal segment is withdrawn into the neuro-catheter and separated from the distal end by a withdrawal distance.

2. The neuro-surgery assembly of claim 1 wherein the portion of the plurality of openings are located on an outer radius of the curved configuration.

3. The neuro-surgery assembly of claim 2 wherein the inner tube protrudes through one of the plurality of openings radially beyond an outer surface of the elongate hollow tube surrounding the one of the plurality of openings when the distal segment is in a curved configuration and the inner tube is pressurized.

4. The neuro-surgery assembly of claim 3 wherein the plurality of openings include a plurality of slots oriented perpendicular to a central axis of the elongate hollow tube.

5. The neuro-surgery assembly of claim 2 wherein a shape of each of the plurality of openings changes responsive to flexure of the distal segment away from a straight configuration.

6. A wire guide comprising:
an elongate hollow tube with a distal segment that defines a plurality of openings arranged in a pattern so that the distal segment is more flexible than a proximal segment of the elongate hollow tube;
an inner tube positioned inside the elongate hollow tube and having a closed distal end;
an inflation device with a reservoir of liquid fluidly connected to a proximal end of the inner tube;
the wire guide having a stiff condition in which the inner tube is pressurized by the liquid causing an external surface of the inner tube to bear against an internal surface of the elongate hollow tube;
the wire guide having a soft condition in which the inner tube is depressurized causing the external surface of the inner tube to be at least partially out of contact with the internal surface of the elongate hollow tube;

wherein the inner tube protrudes into a portion, which is less than all, of the plurality of openings when the distal segment is in a curved configuration and the wire guide is in the stiff condition;

wherein a shape of each of the plurality of openings changes responsive to flexure of the distal segment away from a straight configuration.

7. The wire guide of claim 6 wherein the portion of the plurality of openings are located on an outer radius of the curved configuration.

8. The wire guide of claim 7 wherein the inflatable inner tube protrudes through one of the plurality of openings radially beyond an outer surface of the elongate hollow tube surrounding the one of the plurality of openings when the distal segment is in a curved configuration and the wire guide is in the stiff condition.

9. The wire guide of claim 8 wherein the plurality of openings include a plurality of slots oriented perpendicular to a central axis of the elongate hollow tube.

10. A method of operating a neuro-surgery assembly that includes a wire guide with an elongate hollow tube with a distal segment that defines a plurality of openings arranged in a pattern so that the distal segment is more flexible than a proximal segment of the elongate hollow tube; an inner tube positioned inside the elongate hollow tube and having a closed distal end; the wire guide having a stiff condition in which the inner tube is pressurized by a liquid causing an external surface of the inner tube to bear against an internal surface of the elongate hollow tube; the wire guide having a soft condition in which the inner tube is depressurized causing the external surface of the inner tube to be at least partially out of contact with the internal surface of the elongate hollow tube; the method comprising the steps of:

advancing a wire guide around a turn of a tortuous pathway toward a treatment site in a brain while the wire guide is in the soft condition;

stopping the wire guide in the turn with the distal segment in a curved configuration;

sliding a neuro-catheter over the wire guide toward the turn;

changing the wire guide from the soft condition to the stiff condition when a distal end of the neuro-catheter is proximal to the distal segment, and the stiff condition includes the inner tube protruding into a portion, which is less than all, of the plurality of openings;

sliding the neuro-catheter around the turn and over the distal segment toward the treatment site;

changing the wire guide from the stiff condition back to the soft condition;

stopping the neuro-catheter at the treatment site;

maintaining the neuro-catheter at the treatment site while withdrawing the wire guide in the soft condition from the neuro-catheter.

11. The method of claim 10 including changing the wire guide between the soft condition and the stiff condition a plurality of times during the advancing step.

12. The method of claim 11 including a step of stopping the wire guide at the treatment site.

13. The method of claim 10 wherein the inner tube protrudes through one of the plurality of openings radially beyond an outer surface of the elongate hollow tube surrounding the one of the plurality of openings when the distal segment is in a curved configuration and the wire guide is in the stiff condition.

\* \* \* \* \*